(12) United States Patent
Scherpenborg

(10) Patent No.: US 7,351,217 B2
(45) Date of Patent: Apr. 1, 2008

(54) THERMAL COMPRESSIVE AERATING BANDAGE AND METHODS OF USE RELATING TO SAME

(76) Inventor: Yvette Scherpenborg, 10751 Wilshire Blvd., Ste. 801, Los Angeles, CA (US) 90024

( * ) Notice: Subject to any disclaimer, the term of this patent is extended or adjusted under 35 U.S.C. 154(b) by 131 days.

(21) Appl. No.: 10/848,963

(22) Filed: May 19, 2004

(65) Prior Publication Data

US 2005/0124925 A1    Jun. 9, 2005

Related U.S. Application Data

(60) Provisional application No. 60/320,215, filed on May 23, 2003.

(51) Int. Cl.
*A61F 13/00* (2006.01)
(52) U.S. Cl. ..................... 602/75
(58) Field of Classification Search ............ 602/41–44, 602/57, 59, 62, 75, 76, 26; 607/112
See application file for complete search history.

(56) References Cited

U.S. PATENT DOCUMENTS

| | | | |
|---|---|---|---|
| 3,425,412 A | * | 2/1969 | Pope ................... 602/59 |
| 4,516,572 A | * | 5/1985 | Schlein ................ 602/3 |
| 4,556,055 A | | 12/1985 | Bonner |
| 4,588,400 A | | 5/1986 | Ring et al. |
| 4,592,358 A | | 6/1986 | Westplate |
| 5,160,328 A | | 11/1992 | Cartmell et al. |
| 5,190,033 A | | 3/1993 | Johnson |
| 5,267,952 A | * | 12/1993 | Gardner ................ 602/58 |
| 5,334,646 A | | 8/1994 | Chen |
| 5,431,622 A | | 7/1995 | Pyrozyk et al. |
| 5,531,670 A | | 7/1996 | Westby et al. |
| 5,697,328 A | * | 12/1997 | Hunter ............... 119/714 |
| 5,697,961 A | | 12/1997 | Kiamil |
| 5,887,437 A | | 3/1999 | Maxim |
| 5,994,450 A | | 11/1999 | Pearce |
| 6,528,696 B1 | | 3/2003 | Ireland |
| 2002/0103520 A1 | | 8/2002 | Latham |

* cited by examiner

Primary Examiner—Kim M Lewis
(74) Attorney, Agent, or Firm—Dalina Law Group, P.C.

(57) ABSTRACT

A lightweight, flexible, aerating, compressive, thermal bandage. Perforations allow the treatment area to aerate. Thermal capacity of the invention allows for hot or cold treatment in a manner that compressively supports the object undergoing thermal treatment while maintaining maximum mobility. The bandage is made from an elastomer such as polyeurathane with the addition of silicon and vegetable oil. Resin is used to color the product.

1 Claim, 6 Drawing Sheets

THERMAL COMPRESSIVE AERATING BANDAGE AND METHODS OF USE RELATING TO SAME

This application takes priority to U.S. Provisional Patent Application Ser. No. 60/320,215 filed May 23, 2003, entitled, "Thermal Compressive Aerating Bandage and Methods of Use Relating to Same" which is hereby incorporated herein by reference.

BACKGROUND OF THE INVENTION

Embodiments of the invention relate to the field of medical devices and more particularly to solid elastomers applied to an area of discomfort for purposes of heating or cooling that area.

It is commonplace for people to utilize devices with thermal capacitance to treat an injury or area of discomfort. A hot-cold pack is an example of one such widely utilized device. Cold packs are generally used in order to numb an area and relieve swelling, while hot packs are used to loosen up tight muscles or tendon strains. Many hot-cold packs utilize a gelatinous substance that can undergo state changes in order to provide a higher capacity of heat absorption, i.e., cooling. Such gels may provide similar functionality using water or chemical compounds that initiate changes in state (i.e., liquid to solid). A majority of hot-cold packs and other similar devices store the gel or liquid based substance that provides thermal capacitance in a sealed bag. A problem with this approach is that over time, these bags often leak or otherwise degrade to a point where use is impractical Another issue with using current hot-cold packs is that problems can arise when the treatment area receives little air, as the underlying area can become sweaty and the hot-cold pack can laterally or vertically slide around on the treatment area during movement of the recipient. Thus, in some instances application of the hot-cold pack can further aggravate the injury, or frustrate the wearer to the point of not using the hot-cold pack.

Existing hot-cold packs are designed for use on immobile subjects and generally lack an effective securing mechanism. When the subject of the hot-cold pack treatment is an athlete, animal or a young child or any other entity requiring continued mobility, it is important to adequately secure the pack to the subject. Securing the hot-cold packs is typically achieved by a secondary means. Generally, the packs are held in place with an elastic bandage which limits the mobility of movement of recipient of the pack since the pack may easily become displaced and fall off. In other instances, the packs are held in place within a pouch that acts as a means for immobilizing and securing the pouch to a subject, however the packs are still heavy and even if secured tightly still inhibit mobility due to their weight and thickness.

In certain instances it is desirable to compress the hot-cold pack against the region of treatment. Current hot-cold packs lack the elasticity required to perform such compression. It is, however, possible to use a secondary means, namely by an elastic bandage wound around the hot-cold pack, to compress the hot-cold pack against the region to be treated. Thus, some compression type inventions require a secondary device in order to use the hot-cold pack. This is inconvenient in that a person wishing to apply the hot-cold pack to an area for treatment is required to utilize two items before application of the hot-cold pack can occur. In addition, the elastic properties of straps are known to degrade over time, resulting in a poor compression as the age of the strap increases.

The bandage described in U.S. Pat. No. 5,160,328, filed Nov. 3, 1992 to Cartmell, et al., entitled "Hydrogel bandage" consists of a self-adhesive bandage including a substrate having a two sides and multiple layers including a backing layer which forms the first side of the substrate, and an adhesive layer which forms the second side of the substrate. A hydrogel layer is disposed over the second side of the substrate and is made from a polyurethane hydrogel material for absorbing bodily fluids, including wound exudate. Multiple support layers may be interposed between the substrate and the hydrogel layer to provide the bandage with additional support. Although lightweight, and providing a means for aerating a wound, the bandage is incapable of providing compressive means to bear on the wound since the adhesive layer locks the bandage in place over a treatment area.

The bandage described in U.S. Pat. No. 5,531,670, filed Jul. 2, 1996 to Westby, et al., entitled "Heat Conserving Bandage" consists of a heat conserving bandage to cover human or animal tissue, comprising heat reflecting means, positioned next to the tissue for reflecting heat from the tissue, insulation material means covering said heat reflecting means, and cloth covering the insulation material. The heat reflecting means includes a sandwiched structure of a foil of plastic material adjacent to the tissue, and a second foil bonded thereto. Further cloth means can be inserted between the heat reflecting means the tissue. Suitably, the cloth means and the heat reflecting means are bonded together by sewing or an adhesive to create a pocket for receiving the insulation material. Although lightweight and flexible, the invention described provides no means for aerating the treatment area, and indeed attempts not to aerate a treatment area since it is providing a means to insulate only, and not add or remove heat.

The compress described in U.S. Pat. No. 4,556,055, filed Dec. 3, 1985 to Bonner, entitled "Cold Compress", consists of a bandage defined by a layer of closed cell foam polymeric material sandwiched between and bonded to adjacent layers of fabric. One of the layers of fabric is absorbent with respect to aqueous liquids, such as wound exudate, and is adapted to be in contact with an area of the body. Multiple straps are releasably attached to the bandage to form a compress. The straps facilitate adjustment of the compress, the compress also may possess elongated pockets may be sewn to the fabric layer opposite the absorbent layer for insertion of straps to form a brace or provide for additional cooling. Electrodes are contemplated for providing electrical stimulation. Although allowing for application of a cold pad on a treatment area with a compress, the invention is heavy, thus compromising mobility, and is cloth wrapped in order to absorb aqueous fluids. The bandage also allows for electrical stimulation.

The pad described in U.S. Pat. No. 4,588,400, filed May 13, 1986 to Ring, et al., entitled "Liquid loaded pad for medical applications", consists of wound and burn dressings which are prepared from pellicles, which are a thin film of microbially-produced cellulose obtained, for example, by culturing Acetobacter xylinum. A pellicle having a thickness from about 0.1 to 15 millimeters or greater is processed to replace the culture medium with water or other physiologically compatible liquid. The liquid-loaded pellicle is sterilized prior to its use as a dressing or in other medical applications. The pad is liquid based, is heavy, and therefore does not allow for complete mobility or direct aeration. It also appears to be directed towards immobile burn victims, hence it is not designed to provide a compressive means.

The therapeutic cooling device described in U.S. Patent Application 20020103520, filed Aug. 1, 2002 to Latham, entitled "Therapeutic cooling devices", consists of a thermal regulatory system to reduce swelling caused by trauma to a variety of tissues and limbs. One or more substantially flexible, at least partially thermally conductive housings containing an activatable thermal regulatory medium may be coupled with one or more applicator, such as a splint, that is adapted to apply the thermal source to the tissue. The invention also discloses methods of therapeutically regulating tissue temperature. The invention relates to thermal regulatory systems that are generally heavy gel filled devices that are form fitted for a particular body part not allowing mobility, and providing no means for compressing a treatment area.

The therapeutic pack described in U.S. Pat. No. 5,190, 033, filed May 2, 1993 to Johnson, entitled "Ice peas cold/hot therapeutic pack", consists of an improved cold/hot pack for physiotherapy having a completely sealed flexible pouch. The cavity of the pouch is filled with a plurality of approximately pea sized or larger hollow capsules. The cavities of the hollow capsules are filled with cold/hot storing fluid or gel and are essentially used as a replacement for frozen peas. Partitions prevent migration of the capsules within the pouch and a screened plug permits air to be expelled from the pouch while the capsules are retained in order to conform the pouch to a given body part. The invention appears to be flexible but contains capsules in a pouch that would inhibit mobility when the pouch was strapped on. In addition, the invention would not allow the underlying treatment area to be aerated. The invention appears have no means for applying a compressive force and is directed mainly to cooling of the treatment area solely in a manner mirroring the use of frozen vegetable bags.

The therapeutic device described in U.S. Pat. No. 4,592, 358, filed Jun. 3, 1986 to Westplate, entitled "Therapeutic device", consists of a therapeutic device featuring a plurality of compartments enclosing a therapeutic substance such as a refrigerant material which remains a liquid or forms a slush at temperatures below about 0.degree Celcius, or a heat releasing substance, or a high density material which may be firmly positioned on various body portions using one or more strap means. The invention does not allow for aeration of an underlying treatment area, and uses liquid in order to cool, or a high density material to heat. Each mode of use would not allow for mobility or compression since the device provides non-elastic straps for fastening the device. The device can not be cut for formed into a shape other than that supplied.

The compress described in U.S. Pat. No. 5,697,961, filed Dec. 16, 1997 to Kiamil, entitled "Compress for use in cold and/or hot treatment of an injury", consists of a compress suitable for use in hot and cold treatments of an animal or human body part, comprising a flexible container containing a formulation comprising an aqueous solution and discrete particles of a crosslinked, water-absorbing polymer. In one embodiment, the compress is contained in a sealed plastic bag. The formulation used in the compress can be an anti-freeze agent, a salt compound, a glycol compound or mixtures thereof. The crosslinked, water-absorbing polymer in one embodiment is polyacrylamide or sodium polyacrylate. The invention applies a compressive force to a treatment area, but does not allow for aeration, is heavy, can require an external heat storage unit attached to the compress and is therefore unable to provide mobility. In addition the device cannot be cut to fit a treatment area.

The bandage described in U.S. Pat. No. 5,431,622, filed Jul. 11, 1995 to Pyrozyk et al., entitled "Thermal bandage", consists of a thermal bandage apparatus for simultaneously dressing and thermally treating a wounded area. The device includes a fluid absorbent member having a wound contacting surface for absorbing bodily fluids produced by an open wound and a holding means adjacent and connected to the fluid absorbent member for holding a thermal medium against the fluid absorbent member such that heat is transferred between the thermal medium and the open wound by thermal conduction through the fluid absorbent member. There is also disclosure of an arrangement for providing a continuous supply of heat or cold to a wound. The invention is a non-aerating, and fluid absorbing bandage with associated thermal source pump attached or pouches for the insertion of gel bags. The invention, therefore, does not allow for mobilility, aeration or compression.

The bandage described in U.S. Pat. No. 5,887,437, filed Mar. 30, 1999 to Maxim, entitled "Self-adhering cold pack", consists of a self-adhering cold pack having an envelope defining a sealed cold pack volume. A cooling agent is positioned in the cold pack volume. A bandage sheet is fixed to the envelope by a bandage adhesive. The bandage sheet defines mounting tabs linearly extending from the envelope outer perimeter in order to support a bandage adhesive for temporary adhesion of the cold pack to the skin surface of a patient. The invention does not allow for aeration, is heavy and would not allow for compression of the treatment area.

The bandage described in U.S. Pat. No. 6,528,696 filed Mar. 4, 2003, to Ireland, entitled "Pliable contact bandage", consists of a pliable contact bandage for placement over a wound site located on any skin surface. The apparatus includes a re-openable, flexible enclosure adapted to receive a source of heat or cold, and an adhesive for mounting the pliable contact bandage on a skin surface. The source of heat or cold is temporarily placed within the flexible enclosure and the pliable contact bandage is placed over the wound site in a heat conducting relationship. Typically, a hypo-allergenic adhesive is located along at least a portion of the periphery of the flexible enclosure. The periphery of the flexible enclosure surrounds the wound site. There is no attempt made at enabling mobility or aeration, or compression of the treatment area.

The elastomer described in U.S. Pat. No. 5,334,646, filed Aug. 2, 1994, to Chen, entitled "Thermoplastic elastomer gelatinous articles", consists of novel gelatinous compositions and articles formed from an intimate melt blend admixture of poly(styrene-ethylene-butylene-styrene) triblock copolymer and high levels of a plasticizing oil. The gelatinous composition is transparent and has properties including unexpectedly high elongation and tensile strength and excellent shape retention after extreme deformation under high-velocity impact and stress conditions. The gelatinous products of this invention are soft, flexible, and have elastic memory, characterized by a gel rigidity of from about 20 gram to about 700 gram Bloom. The invention is an elastomer and articles of manufacture based on the gelatinous elastomer. The patent however does not enable the creation of an aerating, mobile embodiment, or enable the manufacture of an embodiment with additives allowing for higher heat capacity.

The elastomer described in U.S. Pat. No. 5,994,450, filed Nov. 11, 1999, to Pearce, entitled "Gelatinous elastomer and methods of making and using the same and articles made therefrom" consists of gelatinous elastomers, methods for making gelatinous elastomers, methods for using gelatinous elastomers, products made from gelatinous elastomers, and products which include gelatinous elastomers as a component or ingredient. More particularly, the invention includes a gelatinous elastomer formed from a combination of a block copolymer of the general configuration A-B-A and a plasticizer. The preferred A-B-A copolymer of the invention is polystyrene-hydrogenated poly(isoprene+butadiene)-polystyrene and the preferred plasticizer is either mineral oil or a combination of mineral oil and resin. Various other components may be included in the preferred recipes according to the invention. This invention includes improvements to Chen's '646 invention, but does not enable the construction of a lightweight, Because of the problems associated with current systems, there is a need for an improved bandage that adequately overcomes the limitations existent in the prior art.

SUMMARY OF THE INVENTION

Embodiments of the invention are directed to a flexible thermal capacitive elastomer configured for use as a bandage. The bandage is designed to retain alterations in temperature so that when applied to an area in need of treatment the bandage changes the temperature of that area while simultaneously aerating and allowing for compression to be applied to the area under treatment. Such abilities are achieved in accordance with one or more embodiments of the invention by molding the bandage into a planar or other form that comprises a set of interspersed perforations that increase the bandage's elasticity and "grip", (i.e., the traction of the bandage perforations that increase the bandage's elasticity and "grip", (i.e., the traction of the bandage however not limited to a particular shape and is intended for use in any dimension that has a suitable purpose. In some instances it is beneficial to vary the total surface area of the bandage so that the bandage effectively covers the treatment area.

Users of the bandage can rapidly adjust the circumference of the bandage by cutting the bandage into any desired shape. Since the bandage is made from a solid material, and is not a liquid based compound held within a pouch the invention eliminates any leakage problems. It is possible to increase or decrease the bandage's heat capacitance by adjusting the thickness to suit possible to increase or decrease the bandage's heat capacitance by adjusting the thickness to suit bandage. Since the bandage comprises a flexible material, the problems existent in the prior art, namely rupturing and other forms of degradation, are overcome.

To provide more or less air flow to the area subject to treatment, the set of interspersed perforations may vary in size and quantity. The perforations may take any shape that allows air to flow to the treatment area. The perforations may, for instance, be geometric or customized to take advantage of a particular niche market. In instances where the target market is identifiable, the perforations may take a form suitable for that market. If, for example, the bandage was intended for use in a children's hospital the perforations (and/or shape of the bandage itself) may intended for use in a children's hospital the perforations (and/or shape of the bandage itself) may One or more embodiments of the invention allow for improved mobility throughout the application of treatment. The bandage may, for instance, contain an adhesive end, VELCRO® attach areas or male extrusions that fit or snap into the perforations in order to secure the bandage to the treatment area while maintaining a compressive force. Readers should note, however, that the invention is not limited to these specific attachment means and contemplates the use of any mechanism able to limit movement of the bandage when applied to the treatment area.

DETAILED DESCRIPTION OF THE INVENTION

Embodiments of the invention are directed to a crosslinked high-polymer materials with elastic behavior (eg., an elastomer) formed for use as a bandage or compression wrap. The bandage is designed to retain alterations in temperature so that when applied to an area in need of treatment the bandage effectuates a change in temperature to that area while simultaneously aerating and allowing for compression to be applied. Thus, the bandage implementing one or more aspects of the invention can, for instance, provide a mechanism for cooling or heating an area of a person or animal that has been injured or is in discomfort. In the case where a user wishes to cold treat an area, the user can cool the bandage by exposing the bandage to a refrigerated environment for a duration of time adequate enough to bring the bandage's refrigerated environment for a duration of time adequate enough to bring the bandage's temperature, the user may apply the bandage to the desired area for purposes of cooling that area. Conversely, by placing the bandage in warm or hot water, the user may apply the bandage to the desired area for purposes of warming that area. Because of the elastic properties of the bandage, users can optionally utilize the bandage to tightly wrap the area being treated and thereby simultaneously apply compression and cold or hot treatment to that area. The solid material retains its elasticity in hot or cold applications and can provide compression in either situation. The bandage may also act as a compressive aerating bandage without the need to effectuate changes in the bandage's surface temperature.

Figure 1:
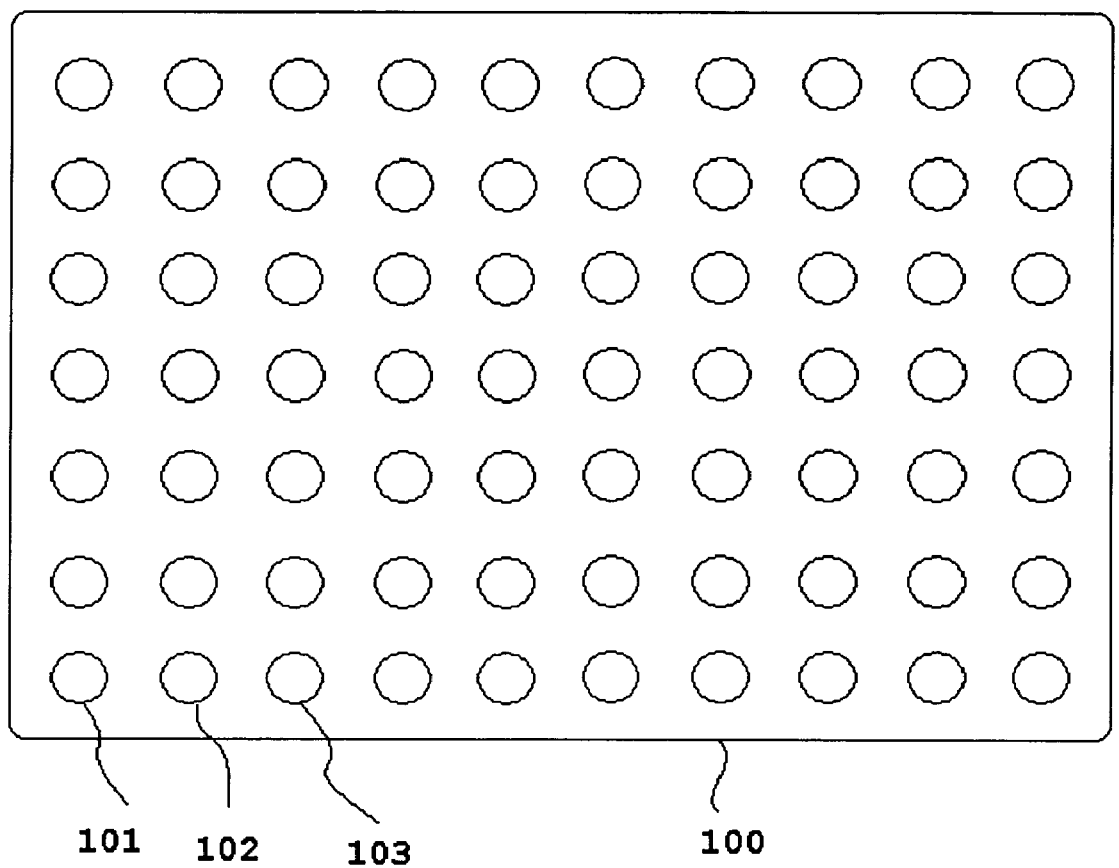
FIG. 1 is a top view of a bandage configured to aerate a treatment area in accordance with an embodiment of the invention.

FIG. 1 depicts a bandage configured in accordance with an embodiment of the invention for use as a compressive wrap. In the example illustrated, the bandage is molded into a planar form 100 that comprises a set of interspersed perforations 101, 102, 103 designed to increase or maintain elasticity while allowing for aeration of the area subject to treatment and compression. In one embodiment of the invention the planar form is achieved via an injection mold process that utilizes an elastomer (e.g., a polyurathane with the addition of silicon and vegetable oil) having properties of thermal capacitance and adequate elasticity. It is important, however, that readers be cognizant of the fact that it is feasible to implement embodiments of the invention using many different types of elastomers or other compounds. Thus, embodiments of the invention include, but are not limited solely to polyurethane elastomers.

It is advantageous to utilize the planar form because such an orientation maximizes the surface area able to contact the treatment area. However, the invention also contemplates the use of other dimensions and can take any shape, thickness, and size suitable to meet a particular need. For instance, using a cutting implement (e.g., scissors, a box cutter, knife, etc . . . ) users may cut the planar form into any shape. Perforations in the material may act as a guide for cutting and users may save material cut away from the planar form for later use as a smaller bandage. The thickness of the bandage can vary from thinner than 1 mm, to thicker than 25 mm, in order to provide solutions for different treatment types. For example a wrap for a wrist could be less than 5 mm thick, while the thickness for an animal leg could be over 25 mm thick. The invention also contemplates the implementation of three-dimensional configurations molded to fit comfortably against a body part.

In one embodiment of the invention, the planar form is composed of a biodegradable compound having a minimal or no toxic effect. Reuse is possible simply by rewashing the bandage thereby making the bandage environmentally friendly. Storage is simplified because it is possible to keep the bandage in the refrigerator or freezer, or stored at room temperature and placed in ice water for quick preparation for cold pack treatment. To use the bandage as a heat pack, a user may fill a hot bucket with water and submerse the bandage into the water.

Figure 2:
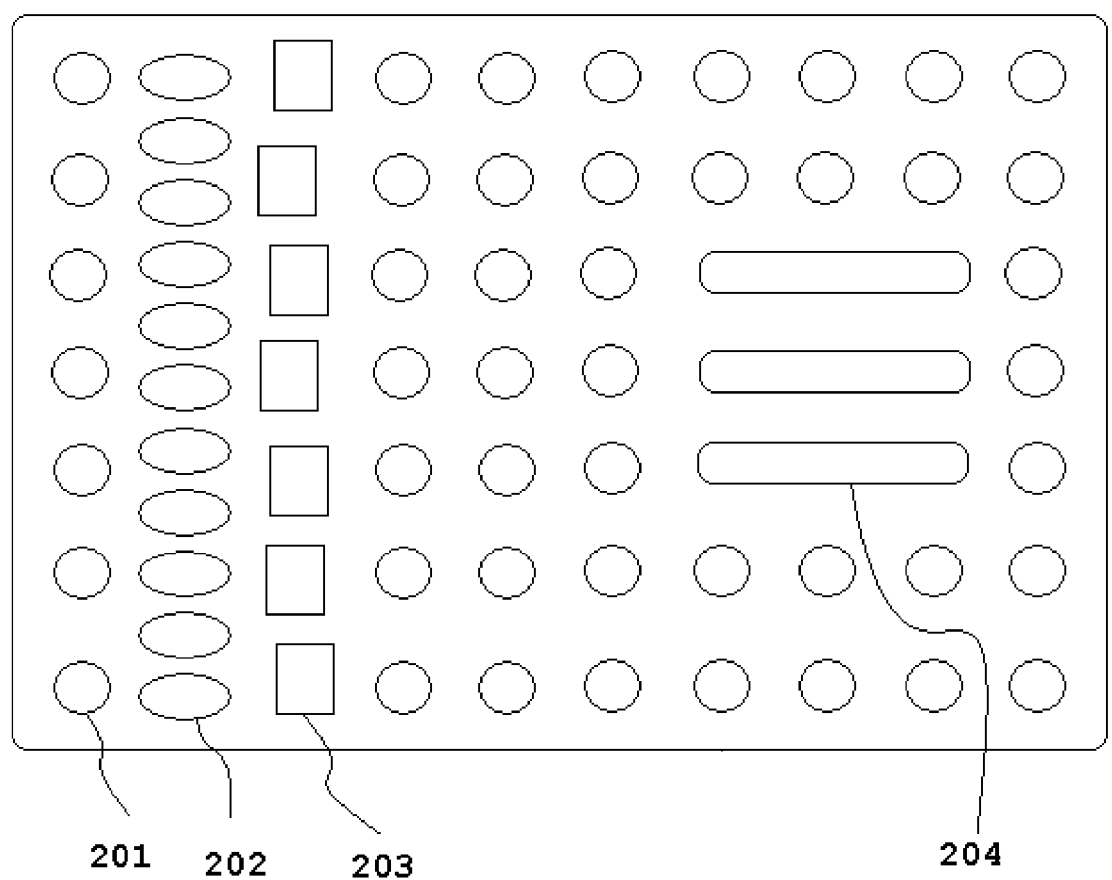
FIG. 2 illustrates an embodiment of the invention with non-uniform placement of perforations.
Figure 3:
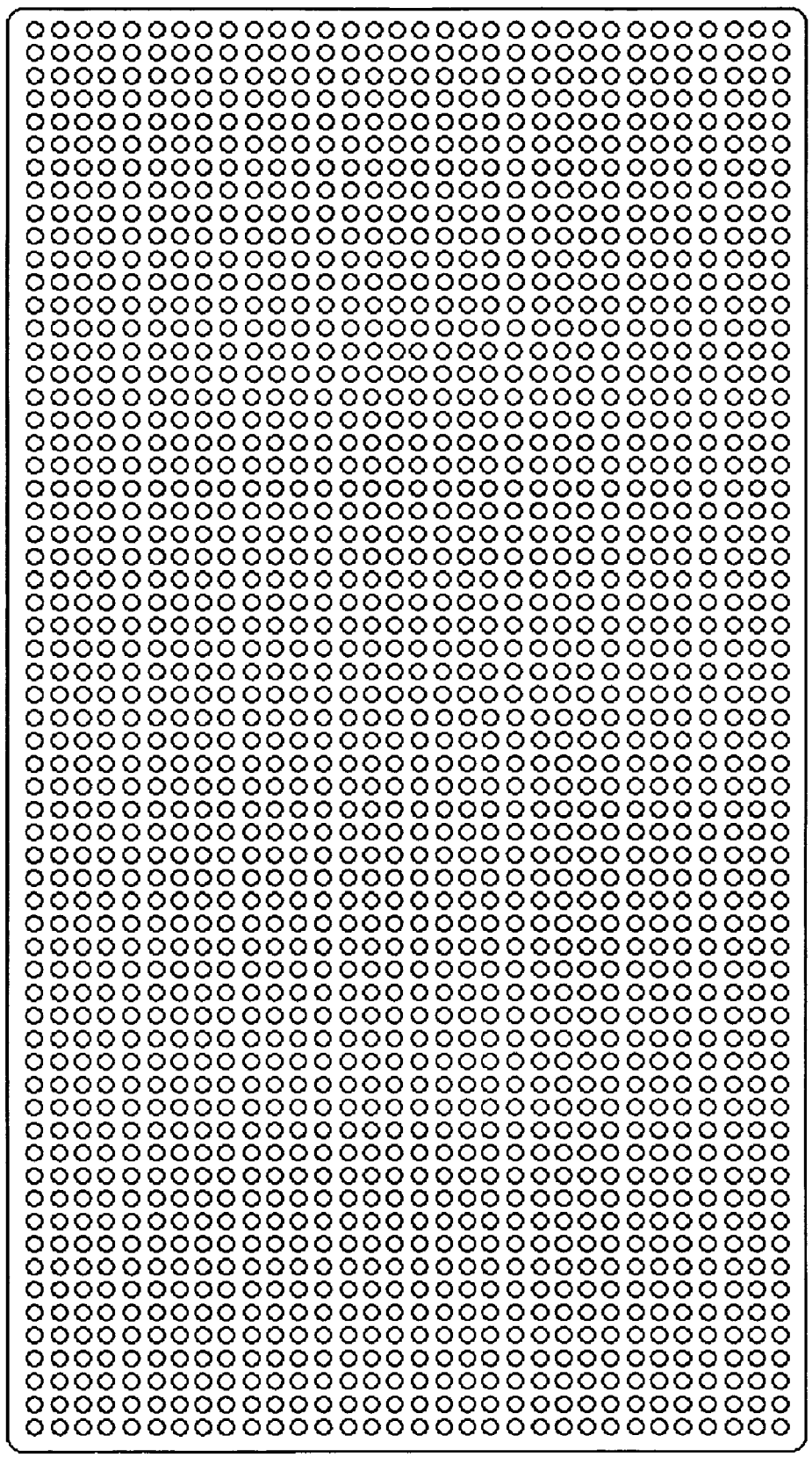
FIG. 3 is a perspective view of an embodiment with male extrusions that fit into the perforations for securing purposes.

The planar form contains a set of interspersed perforations 101-103 that can vary in size and quantity while still providing some level of airflow to the area of treatment. For instance, embodiments of the invention contemplate the use of perforations placed closely or as far away from one another as the particular application requires. Thus, the bandage may contain a set of uniformly or non-uniformly spaced perforations that have consistent or inconsistent diameters and proximity to one another. FIG. 1 illustrates a set of uniformly spaced perforations having consistent diameters whereas FIG. 2 illustrates a set of non-uniformly spaced perforations 201, 202, 203 and 204 having inconsistent shapes, sizes and locations. In instances where aeration of the treatment area is paramount, the bandage may contain bigger perforations than in instances where aeration is less important. The perforations can also have varying shapes and may, for instance, be geometric or customized to take advantage of a particular niche market. In instances where the target market is identifiable, the perforations may take any shape suitable for that market. If, for example, the bandage was intended for use in a children's hospital the perforations (and/or shape of the bandage itself) may take the form of a popular cartoon or other such character.

Figure 5:
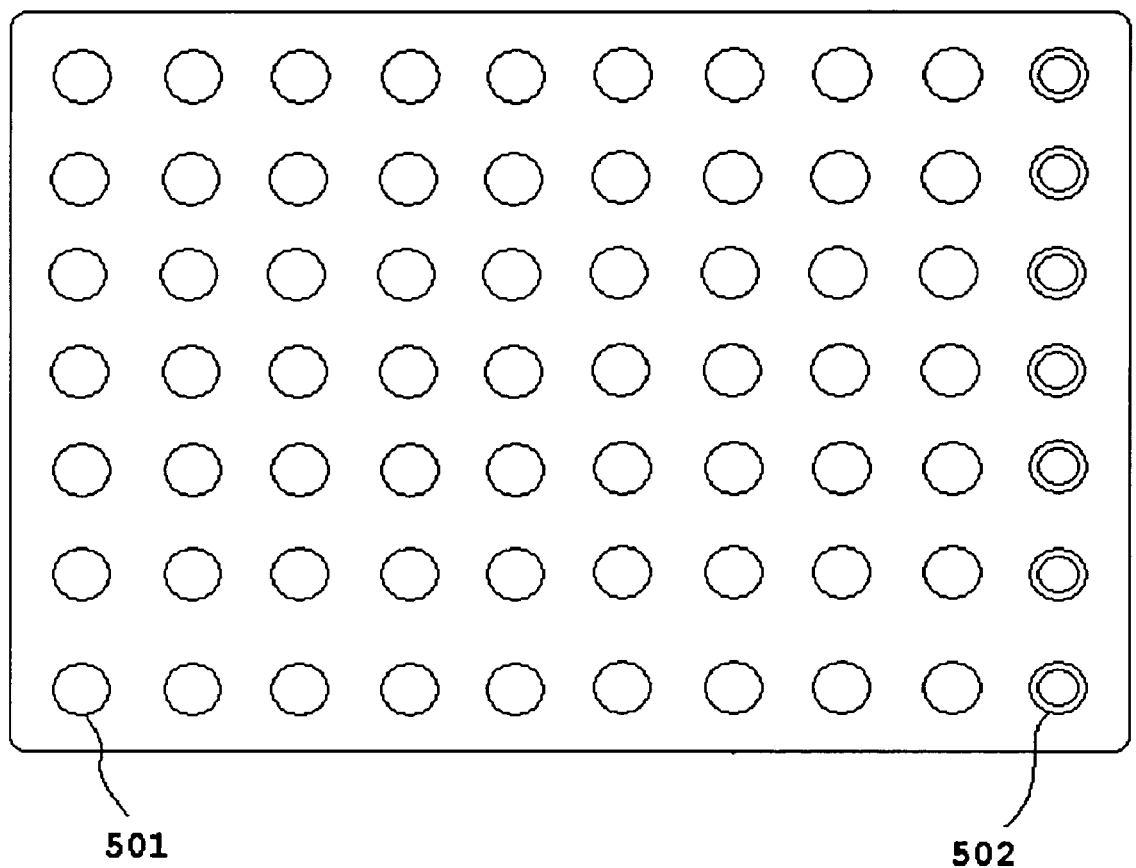
FIG. 5 illustrates an embodiment of the invention for use as an equestrian saddle pad.

FIG. 5 shows an embodiment of invention configured to secure the bandage into a fixed position over the treatment area or extend the bandage to cover a larger surface area. For instance, it is possible to fasten or hook the bandage into longer chains by using snaps 502 that fit into perforations 501. The invention is however not limited explicitly to the use of snaps and contemplates the use of any other type of fastening device able to provide a way to couple bandages together or secure the bandages in place over the treatment area. In other instance, the securing mechanism provides a way to consistently apply a certain amount of compression to the treatment area.

Exemplary Methods of Use:

Embodiments of the invention are applicable for a wide number of uses. Some, but not all of these uses are discussed below for purposes of example. Since it is possible to manufacture the invention in virtually any shape or size the bandage has applicability in any instance where cooling or heating of a surface area is desired. A sunburned person, for instance, might use the bandage as a blanket. By placing the blanket-sized embodiment in a freezer or refrigerator, users can cool the bandage and then wrap it around the patient, thereby providing a soothing relief to the painful effects of the burn.

An embodiment of the invention also has uses as a heat source for someone suffering from cold exposure. For instance, placing a blanket size embodiment in a tub of hot water can act as a means for preheating the blanket prior to arrival of an exposure victim. Once the victim arrives, users can remove the blanket sized embodiment from the water, roll the blanket in a towel to dry it, and wrap the blanket around the victim. Such an implementation enables the victim's skin to breath while maintaining warmth. Wrapping the victim inside a sleeping bag or victim's skin to breath while maintaining warmth. Wrapping the victim inside a sleeping bag or towel provides further insulation from any environmental temperature effects. It is also possible to use the bandage to compression wrap injured limbs with elements cut from the main blanket, or with independently heated or cooled sections. By compressing the bandage over portions of the body, direct contact of the heated bandage can quickly warm the body and bring the victim out of shock.

Figure 6:
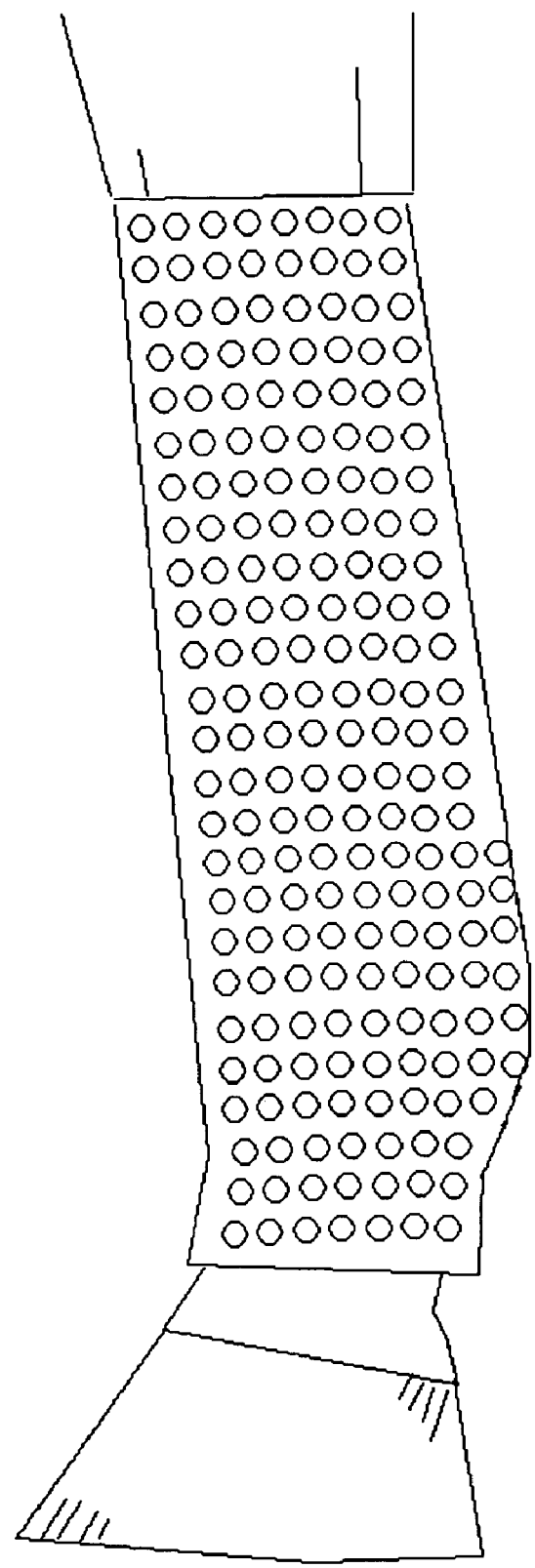
FIG. 6 illustrates an embodiment of the invention for use as an equestrian leg wrap.

FIG. 5 shows an embodiment of the invention which has use as a saddle pad for horses and other animals. By cooling the pad before placement under a horse saddle for instance, the pad can provide a refreshing sensation to the animal. It is also possible to wrap smaller pieces around an animal's leg, either after a race, or after injury. FIG. 6 depicts an embodiment of the invention configured as an equestrian leg wrap. The bandage is wrapped around the treatment area after being cooled to a desired treatment temperature. The bandage cools the treatment area while allowing the animal to freely move. The area under the bandage is highly aerated and this allows the animal to further cool itself via evaporative cooling effects due to sweating. Also, the perforations keep the bandage from sliding around by increasing the grip of the bandage on the treatment area. The perforations further maintain the grip by not allowing excess sweat to build up. The bandage allows the horse to recover faster and this allows the animal to undergo more frequent training sessions for longer periods of time. In addition, the bandage absorbs impact and provides support for tendons and joints in addition to acting as a cold compress.

Figure 4:
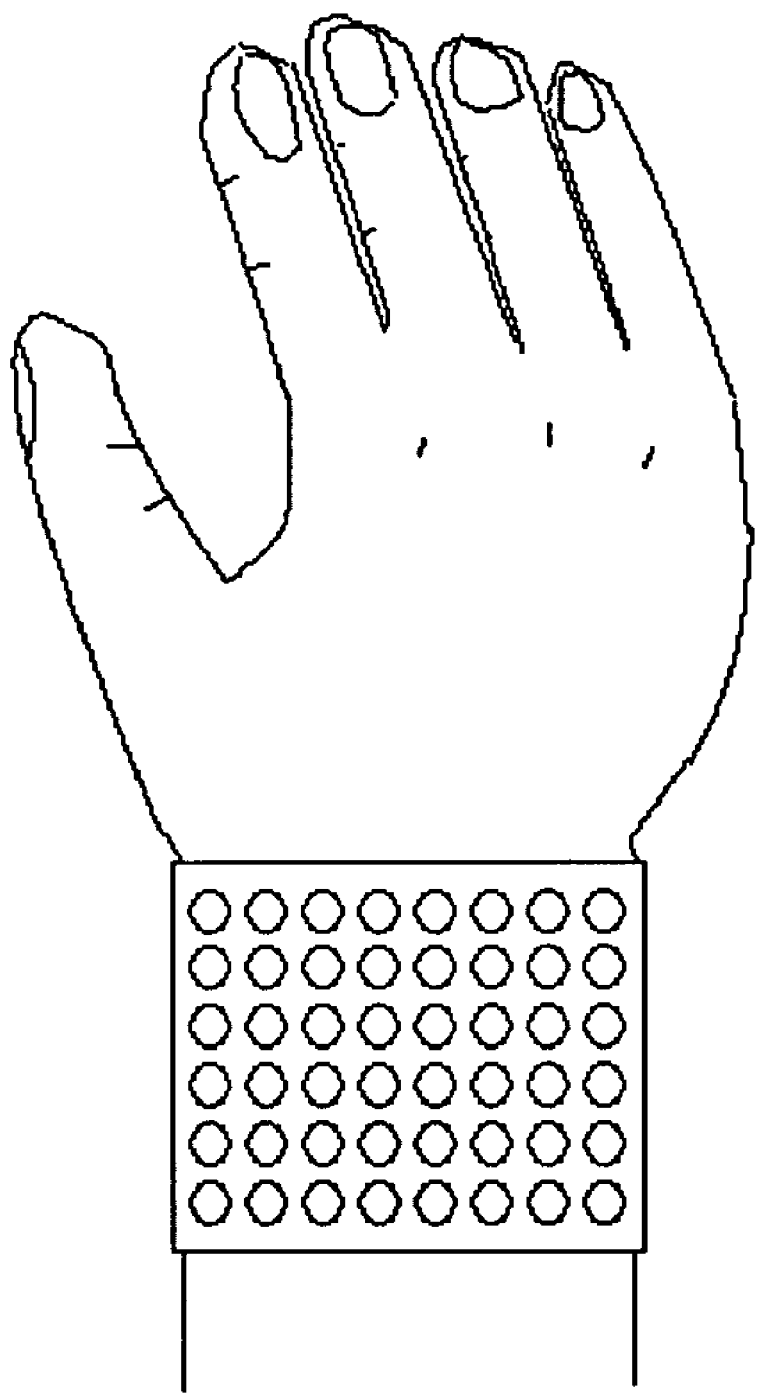
FIG. 4 illustrates an embodiment of the invention for use as a wrist pad.

FIG. 4 depicts an embodiment of the invention either cut from a larger piece to fit the treatment area, or previously manufactured in a smaller format and wrapped around a human wrist. This embodiment provides a padding effect and is suitable for someone with Carpal Tunnel syndrome or other forms of wrist discomfort. When used in the manner depicted, the bandage cools the wrist while simultaneously aerating and padding the wrist thereby easing any discomfort suffered by the wearer.

The bandage also has applications in other medical arenas and can, for instance, provide a soothing compressive, yet aerating wrap for limiting the amount of swelling and bruising caused after surgery or other forms of injury.

Thus a thermal compressive aerating bandage and methods of use relating to same is described. The claims, however, and the full scope of any equivalents are what define the metes and bounds of the invention.

What is claimed is:

1. A bandage configured to enable the application of compressive force to a region of a human being under treatment while simultaneously aerating and cooling or heating said region of treatment, said bandage comprising:

a flexible elastic planar element formed from an elastomer based substance configured to apply compressive force;

said elastomer based substance comprising thermal capacity that allows for hot or cold treatment of said region of treatment;

a plurality of perforations protruding through said flexible planar element where each of said plurality of perforations is for purposes of aerating said region under treatment and increasing said flexible planar element's ability to grip said region of said human being that is undergoing treatment; and, at least one extrusion protruding from at least one portion of said flexible planar element where said at least one extrusion is adapted to secure said bandage over a treatment area of a user by fining into at least one of said plurality of perforations.

* * * * *